(12) United States Patent
Fowler

(10) Patent No.: US 8,716,347 B2
(45) Date of Patent: May 6, 2014

(54) TRAMADOL FOR THE TREATMENT OF FUNCTIONAL GASTROINTESTINAL DISORDERS

(75) Inventor: David Fowler, Cambridge (GB)

(73) Assignee: Euro-Celtique S.A., Luxembourg (LU)

( * ) Notice: Subject to any disclaimer, the term of this patent is extended or adjusted under 35 U.S.C. 154(b) by 671 days.

(21) Appl. No.: 11/443,542

(22) Filed: May 30, 2006

(65) Prior Publication Data

US 2006/0217444 A1 Sep. 28, 2006

Related U.S. Application Data

(63) Continuation of application No. 10/220,544, filed as application No. PCT/GB01/00885 on Mar. 1, 2001, now abandoned.

(30) Foreign Application Priority Data

Mar. 1, 2000 (GB) .................................. 0004998.1
Aug. 25, 2000 (GB) .................................. 0021060.9

(51) Int. Cl.
A61K 31/135 (2006.01)
A61K 31/165 (2006.01)

(52) U.S. Cl.
USPC ............................ 514/646; 514/619; 514/650

(58) Field of Classification Search
USPC ........................................ 514/646, 619, 650
See application file for complete search history.

(56) References Cited

U.S. PATENT DOCUMENTS

| 5,336,691 A | 8/1994 | Raffa et al. |
| 5,738,875 A | 4/1998 | Yarwood et al. |

FOREIGN PATENT DOCUMENTS

| EP | 00189002 | | 7/1986 |
| EP | 307172 | | 3/1989 |
| EP | 0624366 | | 11/1994 |
| EP | 0652879 | | 5/1995 |
| GB | 997399 | | 7/1965 |
| GB | 2111423 | | 7/1983 |
| GB | 2317110 | * | 3/1998 |
| WO | WO-9718801 | * | 5/1997 |
| WO | WO 9718801 | | 5/1997 |
| WO | WO 9840053 | | 9/1998 |
| WO | WO 9942095 | | 8/1999 |
| WO | WO 0051592 | | 9/2000 |
| WO | WO 0115683 | | 3/2001 |
| WO | WO 0134125 | | 5/2001 |

OTHER PUBLICATIONS

Elsing, et al., "Achiral chiral high-performance liquid chromatographic determination of tramadol and its major metabolites in urine after oral administration of racemic tramadol", Journal of Chromatography, 612: 223-230 (1993).
"Irritable Bowel Syndrome (IBS)", UNC Division of Digestive Diseases, UNC School of Medicine, 3 pages, (May 5, 1998).
G. Richard Locke III, MD., "Irritable Bowel Syndrome Research— What is Being Done"; International Foundation for Functional Gastrointestinal Disorders (IFFGD), pp. 1-3 (published in the Spring 1996 edition of *Participate*).
Internet article entitled "Irritable Bowel Syndrome (IBS): IFFGD Members Contribute to Quality of Life Survey", 1 page, (1998).
Bianchi M., et al., "Anti-hyperalgesic effects of tramadol in the rat", *Brain Res*, 797 (1) p. 163-166 (Jun. 22, 1998). Medline abstract No. 98296198.
Bardou M., "Irritable bowel syndrome: From physiopathology to pharmacology", *Rev. Med. Interne*, 1999, 20/2 (151-157). Embase abstract No. 1999406384.
Camilleri M, "Therapeutic approach to the patient with irritable bowel syndrome". *Am. J. Med.*, 1999, 107/5, suppl 1 (27-32). Embase abstract No. 1999404970.
Mitch, et al., "Muscarinic analagesics with potent and selective effects on the gastrointestinal tract: Potential application for the treatment of irritable bowel syndrome", *J. Med. Chem.*, 1997, 40/4 (538-546). Embase abstract No. 1997058806.
Gebhart G.F., "Visceral nociception: Consequences, modulation and the future", *Eur. J. Anaesthesiol. Suppl.*, 1995, 12/10 (24-27). Embase abstract No. 1995166111.
Wiseman, et al., "Cisapride: An updated review of its pharmacology and therapeutic efficacy as a prokinetic agent in gastrointestinal motility disorders", *Drugs*, 1994, 47/1 (116-152). Embase abstract No. 1994041330.
Mascatello, et al., "Irritable bowel syndrome", *J. Am. Osteopath. Assoc.*, 1992, 92/12 (1518-1522). Embase abstract No. 1993005329.
Thompson, et al., "Functional bowel disease and functional abdominal pain" *Gastroenterol. Int.*, 1992, 5/2 (75-91). Embase abstract No. 1992257323.
Roberts-Thomson, et al., "Responses to cholecystokinin octapeptide in patients with functional abdominal pain syndromes", *J. Gastroenterol. Hepatol.*, 1992, 7/3 (293-297). Embase abstract No. 1992174007.
Schafer, et al., "Efficacy and toleration of Buscopan plus, buscopan, paracetamol, and placebo in ambulatory patients with IBS". *Fortschritte der Medizin* 1990, 108/25 (42-44 and 49-50). Embase abstract No. 1990269270.
"Irritable bowel syndrome and its treatment", *Drug and Therapeutics Bulletin*, 1983, 21/10 (37-39). Embase abstract No. 1983133181.

(Continued)

*Primary Examiner* — Sreeni Padmanabhan
*Assistant Examiner* — Shobha Kantamneni
(74) *Attorney, Agent, or Firm* — Davidson, Davidson & Kappel, LLC

(57) ABSTRACT

Tramadol or a pharmaceutically acceptable salt thereof is used in the manufacture of a pharmaceutical preparation for the treatment of functional gastrointestinal disorders such as irritable bowel syndrome.

12 Claims, No Drawings

(56) References Cited

OTHER PUBLICATIONS

Stanciu C., et al.; "Colonic response to pentazocine", *British Medical Journal*, 1974 (312-313). Embase abstract No. 1974184877.

Messaoudi, et al., "Behavioral evaluation of visceral pain in a rat model of colonic inflammation", *NeuroReport*, Apr. 6, 1999, 10/5 (1137-1141. Embase abstract No. 1999238112.

Giamberardino M.A., "Recent and forgotten aspects of visceral pain", *Eur. J. Pain*, 1999, 3/2 (77-92). Embase abstract No. 1999219319.

Morgan G., "Beneficial effects of NSAIDS in the gastrointestinal tract", *Eur. J. Gastroenterol. Hepatol.* Embase abstract No. 1999151863.

Rossel P, et al., "Pain produced by electric stimulation of the rectum in patients with irritable bowel syndrome: further evidence of visceral hyperalgesia", *Scand J Gastroenterol*, Oct. 1999, p. 1001-1006. Medline abstract No. 20025194.

Jones, et al., "Alosetron relieves pain and improves bowel function compared with mebeverine in female nonconstipated irritable bowel syndrome patients", *Aliment Pharmacol Ther*, Nov. 1999, pp. 1419-1427. Medline abstract No. 20039962.

Burke, et al., "Irritable bowel syndrome and recurrent abdominal pain. A comparative review", *Psychosomatics*, Jul.-Aug. 1999, pp. 277-283. Medline abstract No. 99331282.

Goldberg, et al., "Modification of visceral sensitivity and pain in irritable bowel syndrome by 5-HT3 antagonism (ondansetron)", *Digestion*, Nov.-Dec. 1996, p. 478-483. Medline abstract No. 97070783.

Lynn, et al, "Irritable bowel syndrome. Managing the patient with abdominal pain and altered bowel habits", *Med Clin North Am*, Mar. 1997. Medline abstract No. 95182697.

Pharmaceuticals, "FDA approves Glaxo IBS drug", 1 page; Oct. 2, 2002.

Lotronex™ (alosetron hydrochloride) Product Information, Feb. 2000, 14 pages.

"Nightmares and Hallucinations After Long Term Intake of Tramadol Combined with Antidepressants" J. Devulder et al. Acta Clinics Belgica; pp. 184-186; 1996.

Internet article, "Rome II Guidelines for Irritable Bowel Syndrome Diagnosis," http:/www.helpforibs.com/footer/romeguidelines.asp; accessed on Aug. 23, 2005.

Douglass A.Drossman, "The Rome Criteria Process: Diagnosis and Legitimization of Irritable Bowel Syndrome," editorial, The American Journal of Gastroenterology, vol. 94, No. 10, pp. 2803-2807; obtained from http:/www.romecriteria.org/editorials.html on Aug. 23, 2005.

* cited by examiner

TRAMADOL FOR THE TREATMENT OF FUNCTIONAL GASTROINTESTINAL DISORDERS

RELATED APPLICATIONS

This application is a continuation of U.S. application Ser. No. 10/220,544, filed Nov. 18, 2002, which is a national phase filing of International Application No. PCT/GB01/00885, filed Mar. 1, 2001, which claims priority to Great Britain Application Nos. GB 0004998.1, filed Mar. 1, 2000 and GB 0021060.9, filed Aug. 25, 2000.

The treatment of functional gastrointestinal disorders. The present invention relates to the treatment of functional gastrointestinal (GI) disorders, especially irritable bowel syndrome (IBS). In particular the present invention relates to pharmaceutical preparations containing tramadol for the treatment of such disorders and the use of tramadol in the manufacture of such preparations.

BACKGROUND OF THE INVENTION

Tramadol (2-[(Dimethylamino) methyl]-1-(3-methoxyphenyl)cyclohexanol is a non-narcotic opioid analgesic which was first described in the 1960's (see UK Patent 997399). It was first marketed in Germany in 1977 and subsequently in various countries and by 1980 a total of 34 different tramadol formulations in immediate release oral and injectable form were on the market.

In 1996 controlled release preparations containing tramadol were introduced, for example TRAMUNDIN RETARD capsules of Mundipharma GmbH, IRAMAL LONG 100 tablets of Grünenthal GmbH and ZYDOL SR tablets of G D Searle & Co. Ltd. The only medical indication for which the various tramadol products are used is the treatment of moderate to severe pain.

It has been reported that the most-commonly occurring adverse side effects during treatment of pain with tramadol preparations are gastrointestinal upsets. Between one third and a half of patients suffer nausea and vomiting initially when started on tramadol pain therapy.

The most common functional GI disorders are irritable bowel syndrome and non-cardiac chest pain. It is estimated 15-20% of the general population are affected by IBS at some time.

Functional GI disorders are difficult to diagnose as they involve disrupted gastrointestinal function and do not present evidence of organic or physical disease. No routine tests are available to confirm a diagnosis of IBS. However, diagnostic evaluation is often carried out to exclude other potential causes such as colonic cancer or inflammatory bowel disease such as Crohn's disease or ulcerative colitis.

Functional GI disorders are defined and diagnosed by a group of symptoms. For instance, IBS is characterised by a combination of intermittent abdominal pain and diarrhoea, constipation or both; a, or the, principal symptom is pain, which often commences after eating and is relieved by defecation; abdominal distension (bloating) is common. Other symptoms include the passage of mucus and a feeling of incomplete defecation. Clinical studies have indicated that IBS is a disorder affecting the entire GI tract.

The symptoms in IBS are chronic, with remissions and relapse, which may be brought on by stress, food poisoning or changes in bowel flora produced by antibiotics, and they cause discomfort, which, depending on the severity of the disorder, can range from inconvenience to severe distress. For those with severe symptoms, IBS can cause a significant reduction in quality of life to the point where the condition is debilitating.

IBS is not caused by structural, biochemical or infectious abnormalities. Psychological factors have been thought to be important, and more recently specific food intolerances have been implicated.

Patients with IBS exhibit increased gut sensitivity, suggesting that at least part of the problem may be because the nerves that carry information from the gut to the brain, the afferent neurons, produce a response greater than that expected to be produced by the stimuli they have received, which results in non painful stimuli being perceived as painful (visceral hyperalgesia). Antidepressants are thought to affect pain sensation at the spinal level and are used in the treatment of IBS; the antidepressant imipramine was found to increase gut transit time.

IBS is also characterised by abnormal gut motility that is, increased or irregular muscular movement of the gut resulting in diarrhoea, constipation and spasms.

Therapies which are currently used depending on the symptoms presented include dietary fibres i.e. ispaghula husk; antidiarrhoeals such as loperamide; osmotic laxatives; antispasmodics such as hyoscamine and dicyclomine, and dietary supervision if food intolerance is suspected.

For patients with severe pain it is common for mebeverine (which acts on smooth muscle) to be prescribed. However, results are often disappointing and this may lead to the trial of many other remedies of uncertain value, such as antidepressants mentioned above; these are thought to block the transmission of pain signals from the gut to the brain and can sometimes be effective when taken at lower doses than those administered for the treatment of depression.

There is no currently, satisfactory treatment for functional GI disorders.

OBJECT OF THE INVENTION

An aim of the present invention is to provide an alternative therapy for the treatment of functional GI disorder.

SUMMARY OF THE INVENTION

According to one aspect of the present invention we provide the use of tramadol in the manufacture of a medicament for the treatment of functional gastrointestinal disorders. In a particularly preferred embodiment tramadol is used in the manufacture of a medicament for the treatment of irritable bowel syndrome.

According to yet a further aspect of the present invention we provide a pharmaceutical preparation containing tramadol for use in the treatment of functional gastro-intestinal disorder, especially irritable bowel syndrome, in a patient suffering therefrom.

In the treatment of functional GI disorders according to the present invention tranadol is used in an amount of from 10 mg to 800 mg per day, especially 10 mg to 400 mg per day for instance 25 mg to 800 mg or 25 mg to 400 mg per day. Other suitable dosage ranges are 50 mg to 800 mg or 50 mg to 400 mg per day. In the preferred practice of the present invention it is envisaged that a total daily dose of 10 mg to 200 mg, e.g. 25 mg to 200 mg more preferably 25 mg to 100 mg e.g. 25 mg to 50 mg or 50 mg to 100 mg will be used. If given in normal or instant releasing dosing forms this dosage will be divided equally into three, four or six doses given at intervals throughout the day. If given in controlled release form this may be given as a single dose or divided into two separate doses given at spaced intervals.

In the practice of the present invention it is envisaged that suitable controlled release dosage forms e.g. tablets and capsules may be produced according to the methods described in European Patent Application Publications Nos. 0 624 366; 0 642 788, and U.S. Pat. No. 5,955,104, the disclosures of which are incorporated herein by reference.

Normal release dosage forms such as tablets, capsules and drops may be produced by methods conventionally used in the art e.g. as described in Remington's Pharmaceutical Science 16th Edition 1980.

The present invention also envisages the use of instant or rapid releasing formulations in which absorption of the drug may take place sub-lingually or transmucosally, which may e.g. be prepared by methods disclosed in U.S. Pat. No. 5,738,875.

Tramadol can exist in four unique chemical structures; there are two geometrical isomers (which may be referred to herein as diastereoisomers or stereoisomers) cis-tramadol and trans-tramadol in each of which exist two optical isomers (enantiomers). Tramadol which is currently marketed is (1RS,2RS)-tramadol, the individual optical isomers of which are (1R,2R)-Tramadol or (1R,2R)-dimethylaminomethyl-1-(3-methoxyphenyl)cyclohexanol and (1S,2S)-tramadol or (1S,2S)-2-dimethylaminomethyl-1-(3-methoxyphenyl) cyclo hexanol; representing the main geometric isomer, together with a small amount of a mixture of the two other optical isomers.

The other geometric isomer, which is generally found as a minor impurity in Tramadol is (1RS,2SR)-tramadol. The individual optical isomers of this geometric isomer are thus (1R,2S)-Tramadol or (1R,2S)-2-dimethylaminomethyl)-1-(3-methoxyphenyl)cyclohexanol and (1S,2R)-Tramadol or (1S,2R)-2-dimethylaminomethyl)-1-(3-methoxyphenyl)-cyclohexanol.

The present invention includes not only the use of the currently marketed form of tramadol i.e. (1RS,2RS)-Tramadol with a minor amount of (1RS,2SR)-Tramadol, but also the use of individual diastereoisomers and individual enantiomers, and where reference is made in this specification and claims to 'tramadol' this should be understood to mean either a mixture of geometrical isomers or individual geometrical isomers or individual enantiomers or any combination thereof, unless the context indicates otherwise.

It is preferred to use tramadol in the form in which it is currently marketed, that is (1RS,2RS)-Tramadol with a minor amount of (1RS,2SR)-Tramadol, or (1R,2R)-Tramadol or (1S,2S)-Tramadol.

Methods for the preparation of individual diastereoisomers and enantiomers are known in the art. For example, the diastereoisomers can be separated using classical methods such as fractional crystallisation or chromatography in silica or alumina columns; resolution of the enantiomer may be carried out by fractional crystallisation see e.g. Elsing et al in Journal of Chromatography, 612, (1993) 223 and Elsing et al. in Arch. Pharma, 324 (1991) 719, or such resolution may be carried out in known manner using chiral auxiliaries.

Pharmaceutically acceptable salts of tramadol, for use according to the present invention are those conventionally known in the art, such as pharmaceutically acceptable acid addition salts. The hydrochloride salt is particularly preferred.

According to another aspect of the present invention we provide a method of treating functional gastrointestinal disorder, especially irritable bowel syndrome, which comprises administering to a patient suffering from said disorder a pharmaceutical preparation in accordance with the invention as defined above.

In one particular aspect of the practice of the present invention the colicky cramps associated with non-cardiac chest pain are ameliorated; in yet another particular aspect of the practice of the invention one or more of the symptoms associated with IBS as described above, are ameliorated or eliminated.

The present invention also extends to the administration of tramadol in combination with other therapeutic agents, co-administered simultaneously or serially, or preferably in a combination product Some therapeutic classes that might be usefully combined with tramadol for the treatment of IBS are as follows, with some examples of potentially suitable compounds:

Antiemetics—e.g. granisetron, tropisetron, prochlorperazine

Antispasmodics and other drugs altering gut motility—e.g. mebeverine hydrochloride, alverine citrate Gastioprokinetics and motility stimulants—e.g. metoclopramide, domperidone, cisapride Laxatives—e.g. bisacodyl, lactulose Analgesics—e.g. paracetamol, dextropropoxyphene, dihydrocodeine Antidepressants—e.g. amitriptyline hydrochloride, nefazodone, sertraline, venlafaxine Anxiolytics—e.g. diazepam, buspirone, lorazepam Antidiarrhoeal drugs—e.g. loperamide hydrochloride, codeine Antiflatulents—e.g. activated dimethicone.

The prime candidate is mebeverine hydrochloride, typically at a dosage of 135 mg.

The invention is illustrated by the following examples.

EXAMPLES OF THE INVENTION

Example 1

A 31 year old female patient suffering from long term chronic, refractory diarrhoea with severe, persistent abdominal pain was treated with a 50 mg normal release tramadol hydrochloride preparation twice daily. Her condition changed to one of normal bowel movements with absence of pain.

Example 2

A 27 year old female with abdominal pain and diarrhoea responded with normal bowel movements and relief of pain after treatment with 50 mg normal release tramadol twice daily. The only side effect was some drowsiness but the medication was not required to be regularly dosed.

The invention claimed is:
1. A method of treating a symptom of irritable bowel syndrome characterized by a feeling of incomplete defecation, the method comprising:
   ameliorating or eliminating a symptom associated with irritable bowel syndrome in a patient suffering from irritable bowel syndrome by administering from 10 mg to 400 mg of tramadol or a pharmaceutically acceptable salt thereof to said patient per day, wherein the symptom is the feeling of incomplete defecation,
   wherein a single therapeutic agent is administered, said therapeutic agent consisting of said tramadol or a pharmaceutically acceptable salt thereof.

2. The method according to claim 1, wherein the tramadol or pharmaceutically acceptable salt thereof is (1RS,2RS)-tramadol.

3. The method according to claim 1, wherein the tramadol or pharmaceutically acceptable salt thereof is in the form of one of its enantiomers.

4. The method according to claim 1, wherein the pharmaceutically acceptable salt is tramadol hydrochloride.

5. The method according to claim 1, wherein the tramadol is administered in a dosage form selected from the group consisting of a tablet and a capsule.

6. The method according to claim 5, wherein the dosage form is a normal release dosage form.

7. The method according to claim 5, wherein the dosage form is a controlled release dosage form.

8. The method according to claim 1, wherein the tramadol is dosed in an amount of 25 mg to 400 mg, calculated as tramadol hydrochloride, per day.

9. The method according to claim 8, wherein the tramadol is dosed in an amount of 50 mg to 200 mg, calculated as tramadol hydrochloride, per day.

10. The method according to claim 8, wherein the tramadol is dosed in an amount of 50 mg to 100 mg, calculated as tramadol hydrochloride, per day.

11. The method according to claim 8, wherein the tramadol is dosed in an amount of 25 mg to 100 mg, calculated as tramadol hydrochloride, per day.

12. The method according to claim 1, wherein the tramadol is (1RS,2SR)-tramadol or pharmaceutically acceptable salt thereof.

* * * * *